United States Defensive Publication [19] (H) [11] T101,004

Gompf et al. [43] Sep. 1, 1981

[54] BLOCKED PYRAZOLONE MAGENTA DYE-FORMING COUPLERS

[76] Inventors: Thomas E. Gompf; Howell A. Hammond; Jared B. Mooberry, all of Kodak Park Works, Rochester, N.Y. 14650

[21] Appl. No.: 220,579

[22] Filed: Dec. 29, 1980

Related U.S. Application Data

[62] Division of Ser. No. 124,872, Feb. 26, 1980.

[51] Int. Cl.[3] ..... C07D 231/10

[52] U.S. Cl. ..... 548/373; 430/557; 430/558

[57] ABSTRACT

Novel 5-pyrazolone magenta dye-forming couplers are blocked with a coupler moiety which yields an alkali-soluble or colorless reaction product. The coupler moiety is joined via its coupling position to the enol oxygen of the 5-pyrazolone and is displaced therefrom during processing as a result of reaction by means of oxidized color developing agent to thereby activate the 5-pyrazolone coupler. These couplers have good reactivity and good resistance to aerial contaminants, such as formaldehyde, and can be incorporated in photographic emulsions and elements.

5 Claims, No Sheets Drawing,

43 Pages Specification

The file of this unexamined application may be inspected and copies thereof may be purchased (849 O.G. 1221, Apr. 9, 1968).